United States Patent [19]

Hsieh

[11] Patent Number: 4,774,410
[45] Date of Patent: Sep. 27, 1988

[54] ASYMMETRIC S.P.E.C.T. COLLIMATOR WHICH SURROUNDS THE PATIENT

[75] Inventor: Jiang Hsieh, Elk Grove Village, Ill.

[73] Assignee: Siemens Gammasonics, Inc., Des Plaines, Ill.

[21] Appl. No.: 92,016

[22] Filed: Sep. 2, 1987

[51] Int. Cl.⁴ ............................................. G01T 1/166
[52] U.S. Cl. ..................................... 250/363 S; 378/4
[58] Field of Search ................. 250/363 SH, 363 SC, 250/363 SB; 378/19, 10, 4

[56] References Cited

U.S. PATENT DOCUMENTS 4,095,107  6/1978  Genna et al. ................. 250/363 SB

OTHER PUBLICATIONS

Yoshihisa Akiyama et al., "A Study for Increasing the Resolution of the SPECT Image." Japanese Journal of Nuclear Medicine, vol. 24, No. 1 (Jan. 1987), pp. 71–75, as reported in Japanese Technical Abstracts, vol. 2, No. 8 (Aug. 1987), p. 365.

Primary Examiner—Janice A. Howell
Assistant Examiner—Constantine Hannaher
Attorney, Agent, or Firm—Mark H. Jay

[57] ABSTRACT

First, second, third and fourth sections of a collimator are arranged to bound an asymmetric interior region. The collimator has one and only one focal point, which is located inside the body to be imaged. The first and second sections are curved and are preferably circular arcs with different radii of curvature. The third and fourth sections are straight.

5 Claims, 4 Drawing Sheets

ASYMMETRIC S.P.E.C.T. COLLIMATOR WHICH SURROUNDS THE PATIENT

BACKGROUND OF THE INVENTION

Commonly-owned application Ser. No. 28,650 filed Mar. 20, 1987, discloses a collimator and S.P.E.C.T. (single photon emission computerized tomography) scintillation camera system in which there is one and only one focal point and in which that focal point is located inside the body of interest. The imaging process there described proceeds by moving the focal point over the area to be imaged. The entire disclosure of this application is hereby incorporated herein as if fully set forth.

The collimator there disclosed is circular (in the transaxial plane). This is disadvantageous when imaging a patient, because the interior region of the collimator must be large enough to permit the focal point to be traced over all points of the patient's body without collisions between the patient and the inner surface of the collimator. As a result, sensitivity decreases because of the large overall distance between the patient and the inner surface of the collimator.

It would be advantageous to provide a collimator of this type which would have improved sensitivity.

SUMMARY OF THE INVENTION

In accordance with the invention, there is provided a S.P.E.C.T. collimator which is asymmetric in the transaxial plane, bounds an interior region and has one and only one focal point which is located inside the interior region.

Also in accordance with the invention, there are provided first, second, third and fourth collimator sections which are arranged in a closed curve that bounds an interior region. The first and second sections are curved and opposed to each other and the third and fourth sections are straight and opposed to each other. All four sections focus to a single focal point which is located inside the interior region.

A collimator in accordance with the invention bounds an asymmetric interior region. The patient is located at that place within the interior region where the overall distance between the corresponding points on the patient's body and on the inner surface of the collimator is at a minimum and acquisition of the image proceeds with the patient being kept in that location. Advantageously, the collimator is moved about the patient in a polar coordinate system and the patient is held fixed, but this is not required. It is possible to move the collimator in a rectilinear manner and/or to move the patient instead of or in addition to movement of the collimator.

In the preferred embodiment, the most remote curved collimator section is thicker than all the other sections, because tighter collimation is needed as distance between patient and collimator increases.

BRIEF DESCRIPTION OF THE DRAWINGS

Exemplary and non-limiting preferred embodiments of the invention are shown in the drawings, in which.

DETAILED DESCRIPTION OF PREFERRED EMBODIMENTS

Figure 1:
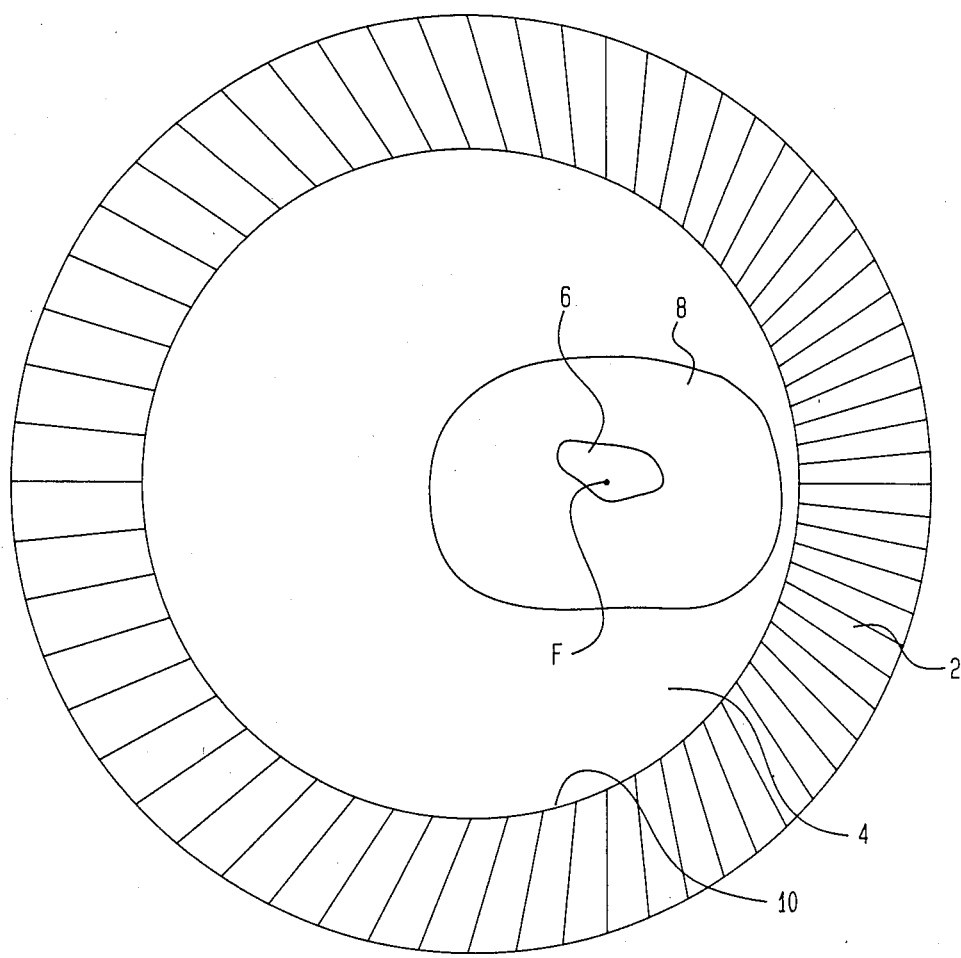
FIG. 1 schematically illustrates the collimator disclosed in a commonly-owned patent application.

In all the Figures, the same or corresponding elements are indicated by the same or corresponding reference numerals. It will be understood that the Figures are all shown in exaggerated scale to illustrate how the collimators focus. Thus, the individual collimator channels are shown much larger than they would actually appear. The same is true for the photodetectors (here, phototubes) shown in the Figures. Additionally, the following description will implicitly assume that the invention is used in a gamma camera which uses NaI(Tl) scintillation material, but this is only preferred and is not essential to the invention. NaI(Tl) is now preferred because it is commonly used, but it is expected that it will be feasible to use CsI(Tl) instead.

The collimator disclosed in the above-referenced commonly-owned copending patent application has a comparatively low sensitivity. This is because its interior region must be comparatively large. This in turn comes about because it is necessary to image not only the region of interest (e.g. the heart) but rather the entire slice of the body in which the region of interest is contained. This is because it is not feasible to acquire a complete set of data of the heart without collecting data about the entire slice of the body which contains the heart; to gather data about the heart alone would cause artifacts to appear in the finished image. (It is unnecessary to image the entire slice of the body with the resolution of the heart, but it is at least necessary to acquire enough data so that the rough location of the heart within the body can be ascertained.)

Figure 2:
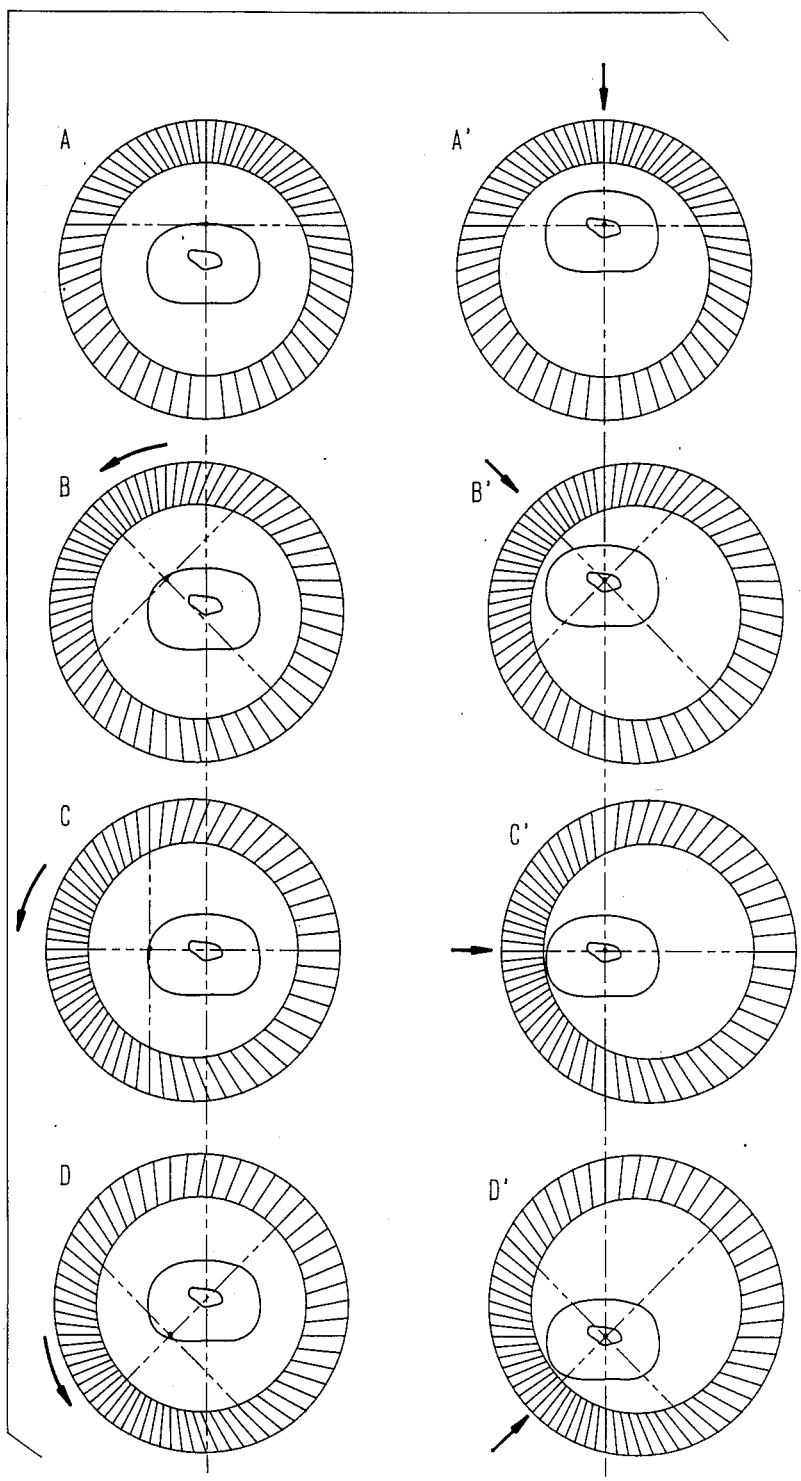
FIG. 2 illustrates why the FIG. 1 collimator has comparatively low sensitivity.
Figure 3:
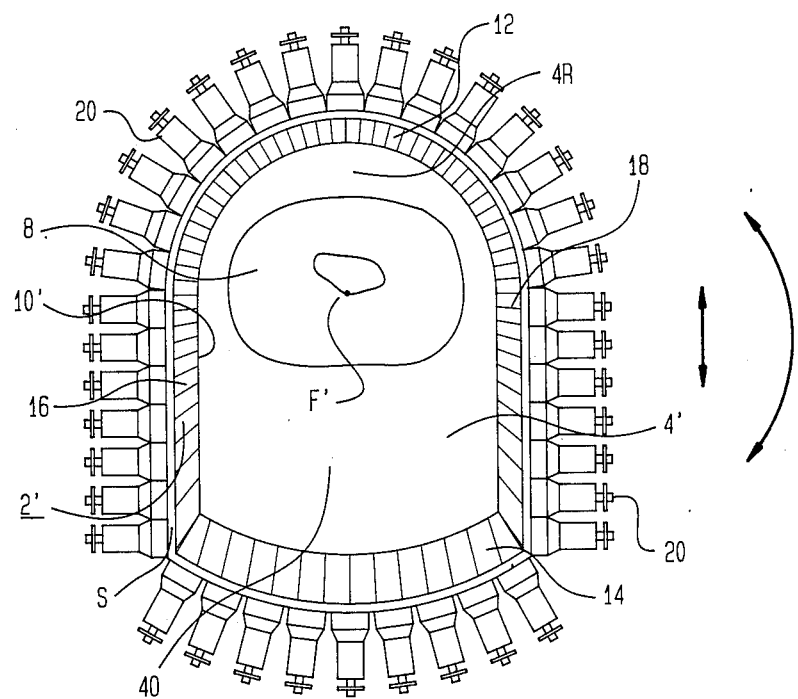
FIGS. 3-6 schematically illustrate different positions of the invention showing how it can be used to image a region of interest.
Figure 4:
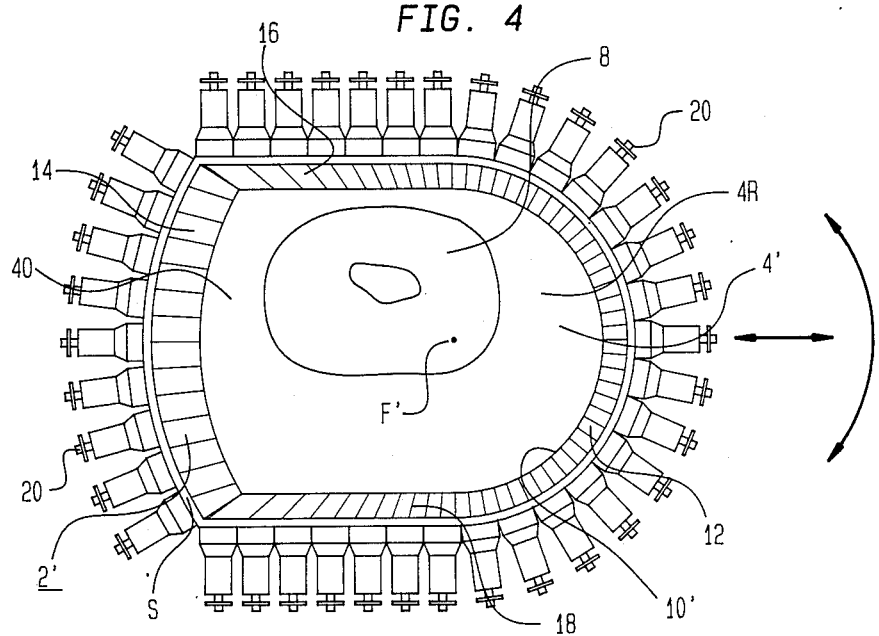
Figure 5:
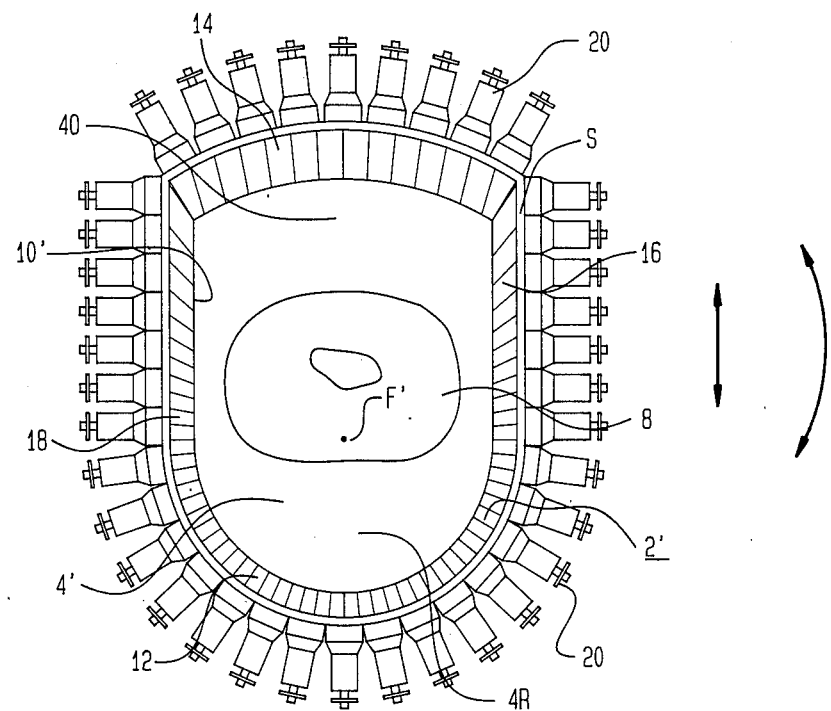
Figure 6:
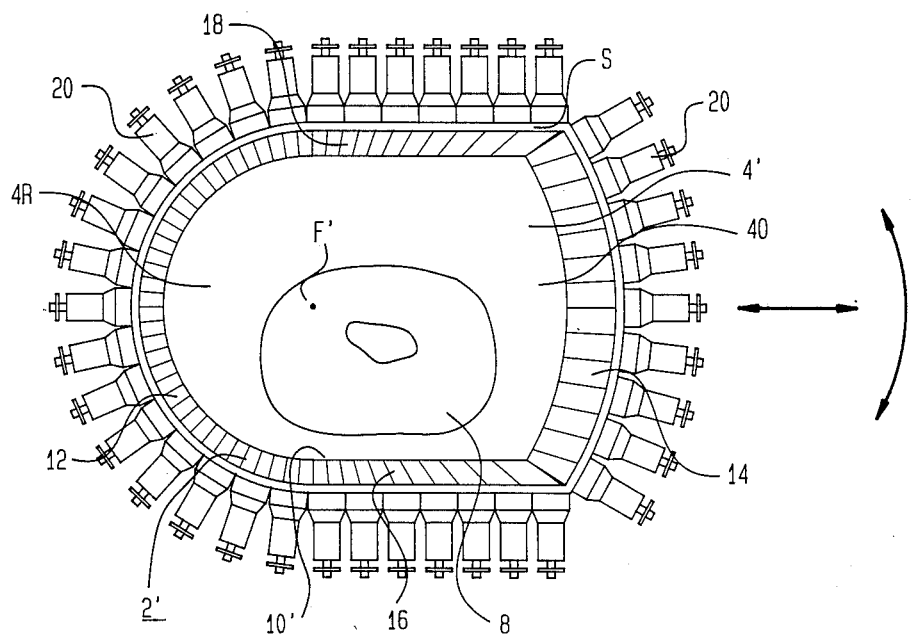

Hence, as is shown in FIGS. 1 and 2, for the collimator 2 to image a patient's heart 6, it is necessary that the focal point F be traced over all of the patient's body 8. To do this, the interior region 4 must be relatively large.

Thus, as can be seen in FIGS. 1 and 2, there is a relatively large overall distance between corresponding points of the inner surface 10 of the collimator 2 and the patient's body 8. As a result of this large distance, the overall sensitivity of the collimator 2 is unnecessarily low.

The preferred embodiment of the invention utilizes the same focusing scheme as in the collimator disclosed in the above-referenced commonly-owned copending patent application. However, the two collimators have different shapes in the transaxial plane. (In the axial plane, the collimators are similar in that there are a plurality of banks of phototubes, each transaxial bank of phototubes corresponding to an image plane of interest.)

The preferred embodiment 2' of the invention is non-circular in the transaxial plane, and has four separate sections 12, 14, 16 and 18 which form a ring and bound an interior region 4'. The first and second sections 12 and 14 of the collimator 2' are curved; advantageously, the first section 12 is shaped as a semicircle and the second section 14 is shaped as a smaller-than-semicircular arc with a larger radius of curvature. The third and fourth sections 16 and 18 are straight. This creates an asymmetric interior region 4' with a rounded end 4R and an oblong end 40. The focal point F' is located in the rounded end 4R.

In use, the patient's body 8 is placed at the rounded end 4R of the interior region 4'. This produces an improved overall sensitivity because the collimator 2' is quite close to the patient's body 8 for most of the points around the periphery of the patient's body 8. As a result, the average distance between corresponding points on the surface of the patient's body 8 and the inner surface 10' of the collimator 2' is less than in the collimator disclosed in the above-referenced, commonly-owned copending patent application.

It will be understood that the collimator 2' is surrounded by a scintillator S and that the scintillator S is surrounded by a plurality of photodetectors (here, phototubes 20) all as described in the above-referenced commonly-owned copending patent application. However, these other components have not been specifically described because they are not part of the invention.

As illustrated, the collimator 2' is of unitary construction but need not be so. Advantageously, the collimator 2' is sectioned so that individual parts thereof may be individually removed and replaced. Such removal and replacement may be necessitated by the need to use a high-resolution collimator as opposed to a low-energy collimator, by the need to use a different radioisotope, or by the need to service a section of the scintillator and/or some of the phototubes. The individual sectioning may correspond to the dividing lines between the sections 12, 14, 16 and 18 or may be otherwise, but this is not a part of this invention.

FIGS. 3-6 are schematic, and are not to scale. The second section 14 of the preferred embodiment is, as illustrated, thicker than the sections 12, 16 and 18. This is because the "tightness" with which radiation is collimated is a function of the length of the channels in the collimator. Because the second section 14 is always most remote from the focal point, it is thicker so that the angular resolution of the second section 14 is appropriately tight.

The illustrations of the relative positions of the phototubes 20 are, like the scale of the channels in the collimator, purely schematic.

Those skilled in the art will understand that changes can be made in the preferred embodiments here described, and that these embodiments can be used for other purposes. Such changes and uses are within the scope of the invention, which is limited only by the claims which follow.

What is claimed is:

1. A collimator for use in SPECT imaging, comprising:
   first, second, third and fourth sections arranged in a manner that
   the first and second sections are curved and opposed to each other and focus to a single focal point;
   the third and fourth sections are straight and opposed to each other and focus to said single focal point; and
   the third and fourth sections are connected to and extend between the first and second sections to form a closed curve which bounds an interior region in which said point is located.

2. The collimator of claim 1, wherein the first and second sections are differently shaped.

3. The collimator of claim 2, wherein the first and second collimator sections are arcs of circles which have different radii of curvature.

4. The collimator of claim 2, wherein a one of the first and second sections is semicircular.

5. A collimator having the shape of a noncircular closed curve, the collimator bounding an interior region and, within each image plane of interest, focusing to one and only one focal point located in said interior region.

* * * * *